United States Patent
Xu et al.

(10) Patent No.: US 12,339,206 B2
(45) Date of Patent: Jun. 24, 2025

(54) TESTING DEVICE FOR CHARACTERISTIC OF RESISTANCE BETWEEN FRESH CONCRETE AND BOUNDARY, AND TESTING METHOD

(71) Applicant: SOUTHEAST UNIVERSITY, Nanjing (CN)

(72) Inventors: Zhisong Xu, Nanjing (CN); Jiaping Liu, Nanjing (CN); Shijun Yuan, Nanjing (CN); Ming Jin, Nanjing (CN)

(73) Assignee: SOUTHEAST UNIVERSITY, Nanjing (CN)

( * ) Notice: Subject to any disclaimer, the term of this patent is extended or adjusted under 35 U.S.C. 154(b) by 0 days.

(21) Appl. No.: 17/928,309

(22) PCT Filed: May 31, 2022

(86) PCT No.: PCT/CN2022/096105
§ 371 (c)(1),
(2) Date: Nov. 29, 2022

(87) PCT Pub. No.: WO2023/082610
PCT Pub. Date: May 19, 2023

(65) Prior Publication Data
US 2024/0280456 A1 Aug. 22, 2024

(30) Foreign Application Priority Data
Nov. 9, 2021 (CN) .......................... 202111318509.7

(51) Int. Cl.
*G01N 33/38* (2006.01)
*G01N 11/14* (2006.01)

(52) U.S. Cl.
CPC ........... *G01N 11/14* (2013.01); *G01N 33/383* (2013.01)

(58) Field of Classification Search
CPC ..... G01N 33/383; G01N 11/14; G01N 11/142; G01N 11/08; G01N 2011/0033
See application file for complete search history.

(56) References Cited

U.S. PATENT DOCUMENTS 3,686,933 A * 8/1972 Sokolov ................. G01N 11/14
 73/843
4,648,264 A * 3/1987 Freese .................... G01N 11/14
 73/64.41

(Continued)

FOREIGN PATENT DOCUMENTS

| CN | 213813257 U | * | 7/2021 |
| CN | 109856001 B | * | 11/2021 |

OTHER PUBLICATIONS

English translation of CN 109856001 (Year: 2021).*
English translation of CN 213813257 (Year: 2021).*

*Primary Examiner* — Tran M. Tran
(74) *Attorney, Agent, or Firm* — CBM PATENT CONSULTING, LLC

(57) ABSTRACT

A testing device for a characteristic of resistance between fresh concrete and a boundary, and a testing method includes a counter-force frame, a driving mechanism, an outer cylinder, a rotor, and pressurization mechanisms, where a bottom of an inner side of the counter-force frame is provided with the driving mechanism, an output shaft of the driving mechanism is connected to the rotor, the rotor is placed in the outer cylinder, space between the rotor and the outer cylinder is filled with a concrete specimen, a plurality of pressurization mechanisms are symmetrically arranged at a top of the concrete specimen, tail ends of the pressurization mechanisms are mounted on the counter-force frame, and the pressurization mechanisms, the rotor and the driving mechanism are connected to a data receiver.

7 Claims, 2 Drawing Sheets

(56) References Cited

U.S. PATENT DOCUMENTS

| | | | | |
|---|---|---|---|---|
| 5,103,679 | A * | 4/1992 | Porter | G01N 33/445 73/54.39 |
| 5,357,785 | A * | 10/1994 | Hemmings | B01L 9/00 73/54.32 |
| 5,948,970 | A * | 9/1999 | Te'eni | B28B 23/0031 73/54.23 |
| 6,691,560 | B2 * | 2/2004 | Abnett | G01N 11/14 73/54.38 |
| 6,997,045 | B2 * | 2/2006 | Wallevik | B01F 35/212 73/54.38 |
| 7,021,123 | B2 * | 4/2006 | Wallevik | G01N 11/14 73/54.38 |
| 7,624,625 | B2 * | 12/2009 | Jau | G01N 33/383 366/64 |
| 7,992,427 | B2 * | 8/2011 | Tonmukayakul | G01N 11/14 73/54.38 |
| 8,375,771 | B1 * | 2/2013 | Bi | G01N 11/14 73/54.33 |
| 8,764,272 | B2 * | 7/2014 | Hazrati | G01N 33/383 700/265 |
| 9,513,201 | B2 * | 12/2016 | Anderson | G01N 11/10 |
| 9,612,232 | B2 * | 4/2017 | Montgomery | G01N 33/383 |
| 9,746,406 | B2 * | 8/2017 | Flock | B08B 9/04 |
| 10,281,450 | B2 * | 5/2019 | Pileggi | G01N 11/14 |
| 10,444,134 | B2 * | 10/2019 | Gajji | G01N 11/14 |
| 10,557,782 | B2 * | 2/2020 | Nowak | G01N 11/162 |
| 11,719,612 | B2 * | 8/2023 | Lee | G01N 11/142 73/54.01 |
| 11,921,022 | B1 * | 3/2024 | Schuetz | G01N 9/14 |
| 12,050,166 | B2 * | 7/2024 | Biesak | G01N 29/032 |
| 12,123,287 | B2 * | 10/2024 | Meeranpillai | E21B 43/12 |
| 12,123,818 | B1 * | 10/2024 | Lu | A62C 37/50 |
| 12,209,939 | B2 * | 1/2025 | Kupzak | G01N 11/162 |
| 2014/0137638 | A1 * | 5/2014 | Liberzon | G01N 11/14 73/54.28 |

* cited by examiner

TESTING DEVICE FOR CHARACTERISTIC OF RESISTANCE BETWEEN FRESH CONCRETE AND BOUNDARY, AND TESTING METHOD

TECHNICAL FIELD

The present disclosure relates to a testing device and a testing method, and in particular to a testing device for a characteristic of resistance between fresh concrete and a boundary, and a testing method.

BACKGROUND ART

Concrete has been widely used since it was invented, and in recent years, with the complication of construction engineering structures, higher demands have been put forward on the working performance of fresh concrete, including terms of fluidity, packing properties, and pumpability of concrete. At a construction site, a resistance action (such as constraints of pump pipes and formworks) of a boundary on concrete has a great influence on both pumping pressure during pumping and packing properties during pouring of the concrete, and therefore, it is important to study a resistance characteristic between fresh concrete and the boundary.

The pumping pressure has long been predicted by using empirical methods, but with the advent of new types of concrete, the rheological properties of the concrete have changed greatly, past experience has been difficult to fully apply, and the predicted pumping pressure tends to deviate greatly from the actual situation. In addition, constraints of resistance of the formworks have a great effect, which is mostly ignored, or no resistance is considered, or no slippage is considered, resulting in a predicted flow distance being too large or too small. There is a large difference between pressure and flow conditions under which fresh concrete is placed in a commonly used slump experiment and the conditions in which the concrete is actually pumped and poured, such that pumpability and packing properties of the concrete fail to be adequately shown. The development of a testing device which is combined with the complexity in practice allows for a more accurate prediction of the working performance such as pumping pressure and packing properties of concrete by taking into account boundary resistances at different pressures and shear slip rates. The working performance and construction production efficiency of fresh concrete are improved by analyzing test data to guide an actual construction production design.

SUMMARY

Disclosure objective: an objective of the present disclosure is to provide a testing device for a characteristic of resistance between fresh concrete and a boundary, and a testing method, which may adjust a shear slip rate between concrete and the boundary, may also adjust pressure states, and may accurately simulate different working conditions of concrete during construction and measure the boundary resistance of the concrete.

Technical solution: the present disclosure includes a counter-force frame, a driving mechanism, an outer cylinder, a rotor, and pressurization mechanisms, where a bottom of an inner side of the counter-force frame is provided with the driving mechanism, an output shaft of the driving mechanism is connected to the rotor, the rotor is placed in the outer cylinder, space between the rotor and the outer cylinder is filled with a concrete specimen, a plurality of pressurization mechanisms are symmetrically arranged at a top of the concrete specimen, tail ends of the pressurization mechanisms are mounted on the counter-force frame, and the pressurization mechanisms, the rotor, and the driving mechanism are connected to a data receiver.

The driving mechanism includes a controller, an electric motor, and a speed reducer, the electric motor is connected to the controller and the speed reducer, an output shaft of the speed reducer is connected to the rotor, and the controller may control output torque of the servo direct current motor and may also control a rotation speed of the servo direct current motor.

The outer cylinder includes an outer cylinder container, an inner wall of the outer cylinder container is provided with anti-slip reinforcing steel bars, and the bottom of the outer cylinder container is provided with a discharge opening which remains closed during a test and may be used to discharge the concrete specimen and dirty water during cleaning after the test is finished, thereby reducing manual labor.

The rotor includes a rotor base plate and rotor side walls, a lower rotor shaft penetrates the rotor base plate, the top of the lower rotor shaft is connected to an upper rotor shaft by means of a torque sensor, and the torque sensor may measure the torque on the rotor side walls.

The upper rotor shaft is connected to the rotor side walls by means of spoke plates.

The rotor base plate is coated with a polytetrafluoroethylene coating which is smooth, wear resistant, and corrosion resistant, and may greatly reduce frictional resistance between the rotor base plate and the rotor side walls.

The lower rotor shaft is connected to the output shaft of the speed reducer via splines which may avoid a slip, thereby effectively transmitting output torque and a rotation speed of the right angle speed reducer to the rotor without loss.

The pressurization mechanisms include a cover plate and jacks, the cover plate is placed on a top of the concrete specimen, the jacks are inverted between the counter-force frame and the cover plate, load cells are arranged between the jacks and the cover plate, and tail ends of the jacks are mounted on a top of the counter-force frame.

A testing method for the testing device for a characteristic of resistance between fresh concrete and a boundary includes the following steps:

step one: assembling components with the exception of the pressurization mechanisms;

step two: casting fresh concrete to be tested into the outer cylinder container, enabling the concrete to be in sufficient contact with the rotor, making a concrete charging height exceed the height of the anti-slip reinforcing steel bars, and smoothing the surface of the concrete specimen;

step three: capping the cover plate, setting up the synchronizing jacks, and arranging the load cells;

step four: enabling all instruments and apparatuses to be connected to a power supply, applying pressure to the concrete specimen by means of the synchronizing jacks, and adjusting the stressed condition of the concrete specimen, where a calculation formula for an average pressure between the concrete and the rotor side walls is as follows:

$$P = \rho g \frac{H}{2} + \frac{F}{\pi(R_2^2 - R_1^2)}$$

in the formula, P is average pressure (kPa) between the concrete and the rotor side walls, $\rho$ is density (g/cm$^3$) of the concrete specimen, g is acceleration of gravity (m/s$^2$), H is height difference (m) between the top face of the concrete specimen and the rotor base plate, F is sum (kN) of external loads applied by the synchronizing jacks, $R_1$ is radius (m) of the rotor, and $R_2$ is radius (m) of the outer cylinder container;

step five: controlling output torque of the servo DC motor by the controller to increase from zero, where a torque value measured by the torque sensor when the rotor starts to rotate corresponds to a yield stress of shear slip resistance at the pressure, a calculation formula for resistance on the boundary is as follows:

$$\tau = \frac{T}{2\pi R_1^2 H}$$

in the formula, $\tau$ is resistance (Pa) on the boundary, and T is torque value (N·m) measured by the torque sensor;

step six: after the rotor starts to rotate, controlling a rotation speed of the servo direct current motor by the controller to obtain the shear slip resistance at the pressure and shear slip rate, wherein a calculation formula for the shear slip rate is as follows:

$$V = 2\pi n R_1$$

in the formula, V is shear slip rate (m/s), and n is rotor rotation speed (rpm);

step seven: repeating step four or step six and drawing resistance-pressure and resistance-rate characteristic curves to obtain the law of variation of boundary resistance at different pressures and shear slip rates.

Beneficial effects: according to the present disclosure, simultaneous adjustment of different pressure states and different shear slip rate conditions may be achieved, different actual working conditions of concrete during construction may be accurately simulated, the resistance between fresh concrete and the boundary at different states is measured, and the law of the resistance characteristic of the boundary under different concrete, different pressures, and shear slip rate conditions may be studied, thereby guiding the design of concrete properties, improving the working performance of concrete and improving the concrete construction techniques; and the influence of device resistance and resistance on the rotor base plate on a measurement result may be eliminated, the measurement accuracy is high, the reliability is strong, the structure is simple, mounting and dismounting is convenient, the applicability range is wide, and the universality is high.

DETAILED DESCRIPTION OF THE EMBODIMENTS

The present disclosure will be further described below with reference to the accompanying drawings.

As shown in FIG. 1 to FIG. 4, the present disclosure includes a counter-force frame, a driving mechanism, an outer cylinder 18, a rotor, and pressurization mechanisms, where a bottom of an inner side of the counter-force frame is provided with the driving mechanism, an output shaft of the driving mechanism is connected to the rotor, the rotor is placed in the outer cylinder 18, space between the rotor and the outer cylinder 18 is filled with a concrete specimen 24, a plurality of pressurization mechanisms are symmetrically arranged at a top of the concrete specimen 24 between the rotor and the outer cylinder 18, tail ends of the pressurization mechanisms are mounted on the counter-force frame, and the pressurization mechanisms, the rotor, and the driving mechanism are connected to a data receiver 28.

Figure 1:
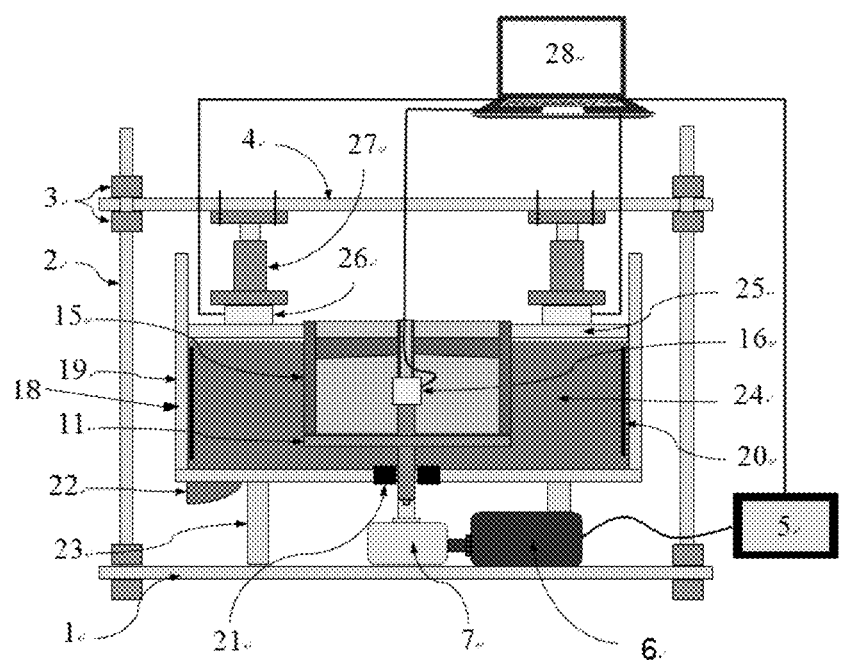
FIG. 1 is a front view of the present disclosure.
Figure 2:
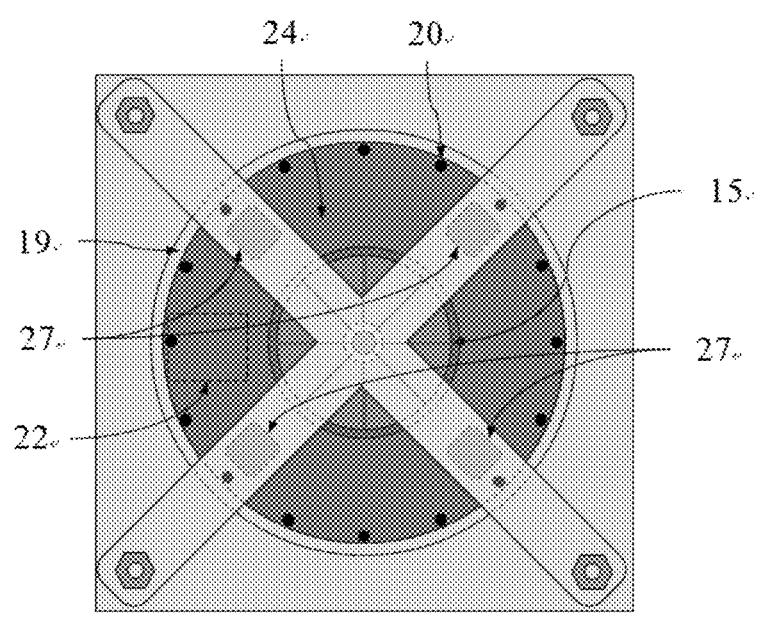
FIG. 2 is a top view of the present disclosure.

As shown in FIG. 1, the counter-force frame includes a base plate 1, screws 2, nuts 3 and a supporting beam 4, and the base plate 1, the screws 2 and the supporting beam 4 jointly form a frame structure, where the four screws 2 are fixed to four corners of the base plate 1 by means of the nuts 3, the supporting beam 4 is fixed to upper portions of the screws 2 by means of the nuts 3 to ensure that the supporting beam 4 is parallel to the base plate 1, and the supporting beam 4 may use either one "X"-shaped beam or one or two "I"-shaped beams or a whole plate, which depends on an actual use case as shown in FIG. 2.

As shown in FIG. 1, the driving mechanism includes a controller 5, a servo direct current motor 6 and a right angle speed reducer 7, where the servo direct current motor 6 and the right angle speed reducer 7 are mounted on the base plate 1, the servo direct current motor 6 is connected to the controller 5 and the right angle speed reducer 7, an output shaft 8 of the right angle speed reducer 7 is connected to the rotor, and the controller 5 may control both output torque of the servo direct current motor 6 and a rotation speed of the servo direct current motor 6, such that control may be conducted according to both torque and the rotation speed in a test. The rotation speed of the servo direct current motor 6 is decelerated by the right angle speed reducer 7 at a rated reduction ratio and then is transmitted to the rotor, and horizontal torque output by the servo direct current motor 6 is converted to vertical torque by the right angle speed reducer 7 and then is output to the rotor. The controller 5 outputs converted real time rotation speed data to the data receiver 28 while controlling the output torque and rotation speed of the servo direct current motor 6, and the servo direct current motor 6 controls its output torque and rotation speed under control of the controller 5 and drives the right angle speed reducer 7 to operate.

Figure 3:
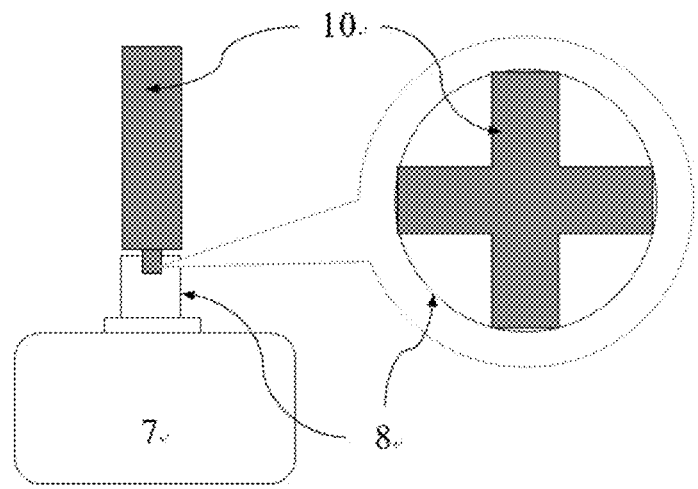
FIG. 3 is a schematic diagram for connection between an output shaft of a speed reducer and a lower rotor shaft in the present disclosure.

As shown in FIG. 3, the output shaft 8 of the right angle speed reducer 7 is connected to a lower rotor shaft 10 of the rotor via splines which avoid a slip, thereby effectively transmitting the output torque and rotation speed of the right angle speed reducer 7 to the rotor without loss. Forms of the splines include, but not limited to, shapes shown in FIG. 3.

As shown in FIG. 1 and FIG. 2, the outer cylinder 18 includes an outer cylinder container 19, anti-slip reinforcing steel bars 20, deep groove ball bearings 21, a discharge opening 22, and supporting columns 23, where the anti-slip reinforcing steel bars 20 are welded to an inner wall of the outer cylinder container 19 and are evenly distributed along the inner wall so as to prevent relative slippage between the concrete specimen 24 and the outer cylinder container 19 during the test and ensure that the rotation speed of the rotor, i.e. the shear slip rate of the concrete specimen 24 and the boundary. The concrete specimen 24 is loaded between the outer cylinder container 19 and the rotor, the concrete specimen 24 should be loaded at a height that exceeds a height of the anti-slip reinforcing steel bars 20 by 1 cm, the deep groove ball bearings 21 are mounted at the center of a base plate of the outer cylinder container 19, and the lower rotor shaft 10 passes through the deep groove ball bearings 21, thereby ensuring that the lower rotor shaft 10 is perpendicular to the base plate of the outer cylinder container 19. The deep groove ball bearings 21 are coated with a cover plate to prevent penetration of cement slurry into the deep groove ball bearings 21 to impede rotation of the rotor. The discharge opening 22 is provided at a bottom of the outer cylinder container 19 and remains closed during the test, and may be used to discharge the concrete specimen 24 and dirty water during cleaning after the test is finished, thereby reducing manual labor. The supporting columns 23 are arranged between the bottom of the outer cylinder container 19 and the base plate 1, support the outer cylinder container 19 and the concrete specimen 24 inside the outer cylinder container, and reserves mounting space for the servo direct current motor 6 and the right angle speed reducer 7.

Figure 4:
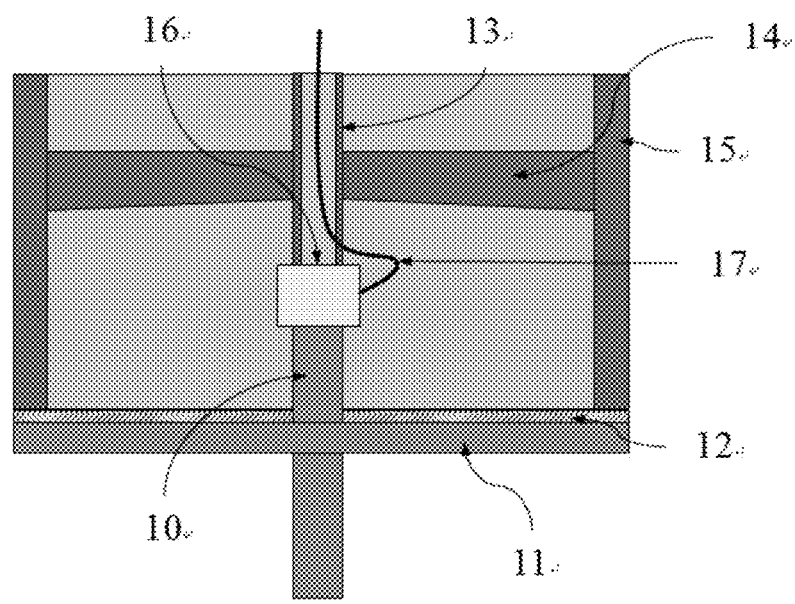
FIG. 4 is a schematic diagram for assembly of a rotor in the present disclosure.

As shown in FIG. 4, the rotor includes the lower rotor shaft 10, a rotor base plate 11, a polytetrafluoroethylene coating 12, an upper rotor shaft 13, spoke plates 14, rotor side walls 15, and a torque sensor 16. Main body components of the rotor are the rotor base plate 11 and the rotor side walls 15, and the lower rotor shaft 10 is a solid shaft that passes through the center of the rotor base plate 11 and remains perpendicular to the rotor base plate. The rotor side walls 15 are connected to the upper rotor shaft 13 by means of the spoke plates 14, and the upper rotor shaft 13 is a hollow shaft. The lower rotor shaft 10 and the upper rotor shaft 13 are connected by means of the torque sensor 16, the torque sensor 16 may measure torque on the rotor side walls 15, and the torque is caused solely by the boundary resistance acting on the rotor side walls 15. An upper surface of the rotor base plate 11 is coated with the polytetrafluoroethylene coating 12, the polytetrafluoroethylene coating 12 is smooth, wear resistant and corrosion resistant and may greatly reduce frictional resistance between the rotor base plate 11 and the rotor side walls 15, and the polytetrafluoroethylene coating 12 may also prevent cement slurry from penetrating into the rotor.

As shown in FIG. 1 and FIG. 2, the pressurization mechanisms include a cover plate 25, load cells 26 and synchronizing jacks 27, where the cover plate 25 is a circular cover plate with an inner circle radius 1 mm larger than a radius of the rotor and an outer circle radius 1 mm smaller than a radius of the outer cylinder container 19, i.e., it is ensured that the cover plate 25 may smoothly pass through the rotor to cover the concrete specimen 24 under test and may also avoid the cement slurry from being squeezed out of gaps during pressurization. Prior to placement of the cover plate 25, a surface of the concrete specimen 24 should be suitably smeared, such that external loads may be evenly exerted on the concrete specimen 24. The synchronizing jacks 27 are inverted between the supporting beam 4 and the cover plate 25, the load cells 26 are arranged between the synchronizing jacks 27 and the cover plate 25 and measure real-time loads applied by the synchronizing jacks 27 on the cover plate 25. One ends of the synchronizing jacks 27 are fixed at a lower bottom surface of the supporting beam 4, and the other ends are free. The free ends of the synchronizing jacks 27 abut against the load cells 26 when the loads are applied, and the synchronizing jacks 27 may achieve the effect that the loads applied to a plurality of jacks keep consistent so as to avoid tilting of the cover plate caused by uneven loads.

As shown in FIG. 1, the controller 5, the torque sensor 16, and the load cells 26 are all connected to the data receiver 28 by means of a shielded wire cable 17. The controller 5 inputs the real-time rotation speed of the rotor, the torque sensor 16 inputs the real-time torque on the rotor side walls 15, and the load cells 26 input real-time magnitudes of external loads exerted on the concrete specimen 24. The shielded wire cable 17 may avoid interference from outside signals on output data, thereby ensuring stable and reliable test data.

A testing method for the present disclosure specifically includes the following steps:

step one: firstly, assemble components with the exception of the pressurization mechanisms;

step two: load fresh concrete to be tested into the outer cylinder container, enable the concrete to be in sufficient contact with the rotor, make a concrete charging height exceed a height of the anti-slip reinforcing steel bars by not smaller than 1 cm, and smooth a surface of the concrete specimen;

step three: cap the cover plate, set up the synchronizing jacks, and arrange the load cells;

step four: enable all instruments and apparatuses to be connected to a power supply, apply pressure to the concrete specimen by means of the synchronizing jacks, and adjust the stressed condition of the concrete specimen, where a calculation formula for an average pressure between the concrete and the rotor side walls is as follows:

$$P = \rho g \frac{H}{2} + \frac{F}{\pi(R_2^2 - R_1^2)}$$

in the formula, P is average pressure (kPa) between the concrete and the rotor side walls, $\rho$ is density (g/cm$^3$) of the concrete specimen, g is acceleration of gravity (m/s$^2$), His height difference (m) between the top face of the concrete specimen and the rotor base plate, F is sum (kN) of external loads applied by the synchronizing jacks, $R_1$ is radius (m) of the rotor, and $R_2$ is radius (m) of the outer cylinder container;

step five: control output torque of the servo direct current motor by the controller to increase from zero, where a torque value measured by the torque sensor when the rotor starts to rotate corresponds to a yield stress of shear slip resistance at the pressure, a calculation formula for resistance on the boundary is as follows:

$$\tau = \frac{T}{2\pi R_1^2 H}$$

in the formula, $\tau$ is resistance (Pa) on the boundary, and T is torque value (N·m) measured by the torque sensor;

step six: after the rotor starts to rotate, control the rotation speed of the servo direct current motor by the controller to obtain the shear slip resistance at the pressure and shear slip rate, where a calculation formula for the shear slip rate is as follows:

$$V = 2\pi n R_1 \qquad 5$$

in the formula, V is shear slip rate (m/s), and n is rotor rotation speed (rpm); and step seven: repeat step four or step six and draw resistance-pressure and resistance-rate characteristic curves to obtain the law of variation of boundary resistance at different pressures and shear slip rates.

What is claimed is:

1. A testing device for a resistance between a concrete and a wall, comprising a counter-force frame, a driving mechanism, an outer cylinder (18), a rotor, and a plurality of pressurization mechanisms, wherein a bottom of an inner side of a counter-force frame is provided with the driving mechanism, an output shaft of the driving mechanism is connected to the lower shaft (10) of the rotor, the rotor is placed inside the outer cylinder (18), space between the rotor and the outer cylinder (18) is filled with a concrete specimen (24); the pressurization mechanisms are symmetrically arranged at a top of the concrete specimen (24), tail end of each of the plurality of pressurization mechanisms is mounted on the upper portion of the counter-force frame, wherein axial load is applied vertically downward to the concrete specimen; the counter-force frame is structurally fixed with the outer cylinder (18) through supporting columns (23), thereby forming an integrated load-bearing system to restrain radial expansion and ensure stable pressurization; and the plurality of pressurization mechanisms, the rotor and the driving mechanism are connected to a data receiver (28); and the rotor comprises a rotor base plate (11) and rotor side walls (15), a lower rotor shaft (10) penetrates the rotor base plate (11), a top of the lower rotor shaft (10) is connected to an upper rotor shaft (13) by means of a torque sensor (16), and the upper rotor shaft (13) is connected to the rotor side walls (15) by means of spoke plates (14).

2. The testing device according to claim 1, wherein the driving mechanism comprises a controller (5), an electric motor, and a speed reducer, the electric motor is connected to the controller (5) and the speed reducer, and an output shaft (8) of the speed reducer is connected to the rotor.

3. The testing device according to claim 1, wherein the outer cylinder (18) comprises an outer cylinder container (19), an inner wall of the outer cylinder container (19) is provided with anti-slip reinforcing steel bars (20), and a bottom of the outer cylinder container is provided with a discharge opening (22).

4. The testing device according to claim 1, wherein the rotor base plate (11) is coated with a polytetrafluoroethylene coating (12).

5. The testing device according to claim 4, wherein the lower rotor shaft is connected to the output shaft of the speed reducer via splines.

6. The testing device according to claim 4, wherein the pressurization mechanisms comprise a cover plate (25) and jacks, the cover plate (25) is placed on a top of the concrete specimen (24), the jacks are inverted between the counter-force frame and the cover plate (25), load cells (26) are arranged between the jacks and the cover plate (25), and tail ends of the jacks are mounted on a top of the counter-force frame.

7. A method for testing the resistance between the concrete and the wall with the testing device of claim 1, comprising the following steps:

step one: assembling the counter-force frame, the driving mechanism, the outer cylinder (18) and the rotor;

step two: casting the concrete to be tested into the outer cylinder container, enabling the concrete to be in sufficient contact with the rotor side walls (15), making a concrete charging height exceed the height of anti-slip reinforcing steel bars, and smoothing the surface of the concrete specimen;

step three: capping the cover plate, setting up synchronizing jacks, and arranging load cells;

step four: enabling all instruments and apparatuses, including the torque sensor, rotation speed controller, load cells, data acquisition system, and servo DC motor, to be connected to a power supply; applying pressure to the concrete specimen by means of the synchronizing jacks, and adjusting stressed condition of the concrete specimen, wherein an average pressure between the concrete and the rotor side walls is calculated as follows:

$$P = \rho g \frac{H}{2} + \frac{F}{\pi(R_2^2 - R_1^2)}$$

in the formula, P is average pressure (kPa) between the concrete and the rotor side walls, $\rho$ is density (g/cm$^3$) of the concrete specimen, g is acceleration of gravity (m/s$^2$), H is height difference (m) between top face of the concrete specimen and the rotor base plate, F is sum (kN) of external loads applied by the synchronizing jacks, $R_1$ is radius (m) of the rotor, and R2 is radius (m) of outer cylinder container;

step five: controlling output torque of servo direct current motor by a controller to increase from zero, wherein a torque value measured by the torque sensor when the rotor starts to rotate corresponds to a yield stress of shear slip resistance at the pressure, the resistance on the wall is calculated as follows:

$$\tau = \frac{T}{2\pi R_1^2 H}$$

in the formula, t is resistance (Pa) on the wall, and T is torque value (N·m) measured by the torque sensor;

step six: after the rotor starts to rotate, controlling a rotation speed of the servo direct current motor by the controller to obtain the shear slip resistance at the pressure and shear slip rate, wherein the shear slip rate is calculated as follows:

$$V = 2\pi n R_1$$

in the formula, Vis shear slip rate (m/s), and n is rotor rotation speed (rpm);

step seven: repeating step four or step six under different pressures and rotational speeds; for each test condition, calculating the average pressure and the shear slip rate based on the predefined formulas, and obtaining the corresponding resistance according to the predetermined torque-based resistance formula; then, plotting resistance-pressure and resistance-rate characteristic curves by using the calculated data; the law of variation of wall resistance with respect to different pressures and shear slip rates is then determined based on the trends observed in the resistance-pressure and resistance-rate characteristic curves.

\* \* \* \* \*